United States Patent
Luo et al.

(10) Patent No.: US 11,260,144 B2
(45) Date of Patent: Mar. 1, 2022

(54) TWO-PASTE CEMENT-FORMING COMPOSITIONS

(71) Applicant: OssDsign AB, Uppsala (SE)

(72) Inventors: Jun Luo, Uppsala (SE); Håkan Engqvist, Uppsala (SE); Cecilia Persson, Uppsala (SE)

(73) Assignee: OSSDSIGN AB, Uppsala (SE)

( * ) Notice: Subject to any disclaimer, the term of this patent is extended or adjusted under 35 U.S.C. 154(b) by 285 days.

(21) Appl. No.: 16/417,795

(22) Filed: May 21, 2019

(65) Prior Publication Data
US 2019/0351096 A1    Nov. 21, 2019

Related U.S. Application Data

(60) Provisional application No. 62/674,195, filed on May 21, 2018.

(51) Int. Cl.
| | | |
|---|---|---|
| *A61L 24/02* | (2006.01) | |
| *A61L 27/36* | (2006.01) | |
| *A61M 5/19* | (2006.01) | |
| *A61B 17/88* | (2006.01) | |

(52) U.S. Cl.
CPC .......... *A61L 24/02* (2013.01); *A61B 17/8833* (2013.01); *A61L 27/365* (2013.01); *A61B 2017/8838* (2013.01)

(58) Field of Classification Search
CPC .......... A61L 24/02; A61L 27/365; A61M 5/19
See application file for complete search history.

(56) References Cited

U.S. PATENT DOCUMENTS

| | | | |
|---|---|---|---|
| 6,994,726 B2 * | 2/2006 | Lin | ........................... A61F 2/28 |
| | | | 264/250 |
| 8,709,149 B2 | 4/2014 | Engqvist et al. | |
| (Continued) | | | |

FOREIGN PATENT DOCUMENTS

WO    2014/091469 A1    6/2014

OTHER PUBLICATIONS

Aberg, J et al., Premixed Acidic Calcium Phosphate Cement: Characterization of Strength and Microstructure, Journal of Biomedical Materials Research, vol. 93B, No. 2, pp. 436-441 (May 1, 2010).

(Continued)

*Primary Examiner* — Nicholas W Woodall
(74) *Attorney, Agent, or Firm* — Porter Wright Morris & Arthur LLP

(57) ABSTRACT

Injectable, ready-to-use two-paste cement-forming compositions comprise a first paste and a second paste. The first paste comprises a non-aqueous oil-based suspension of monocalcium phosphate monohydrate (MCPM) powder, at least one surfactant effective to improve compatibility of the oil and the MCPM, and an organic acid, with an oil to MCMP powder weight ratio of about 0.2 to about 0.5. The second paste comprises an aqueous suspension of β-tricalcium phosphate (β-TCP) powder and a gel-forming polymer, with a water to β-TCP powder weight ratio of about 0.3 to about 0.5. The molar ratio of β-TCP powder to MCPM powder is greater than 1. An article of manufacture comprises a first compartment in which the first paste is contained, and a second compartment in which the second paste is contained. The compositions are useful for bone repair or replacement.

19 Claims, 6 Drawing Sheets

(56) References Cited

U.S. PATENT DOCUMENTS

| | | |
|---|---|---|
| 9,206,080 B2 | 12/2015 | Engqvist et al. |
| 9,259,439 B2 | 2/2016 | Chow et al. |
| 9,540,280 B2 | 1/2017 | Engqvist et al. |
| 2002/0155144 A1* | 10/2002 | Troczynski .......... A61K 9/1694 424/423 |
| 2004/0068266 A1* | 4/2004 | Delmotte ........... A61B 17/8833 606/92 |
| 2008/0299093 A1* | 12/2008 | Yang .................. A61L 24/0042 424/93.7 |
| 2009/0048145 A1* | 2/2009 | Hellerbrand ............ A61P 19/08 514/1.1 |
| 2009/0254194 A1* | 10/2009 | Peters ..................... A61L 27/50 623/23.61 |

OTHER PUBLICATIONS

Luo, Jun et al., A ready-to-use acidic, brushite-forming calcium phosphate cement, Acta Biomaterialia, vol. 81, pp. 304-314 (Oct. 4, 2018).

Engstrand, M.D., Thomas et al., Development of a bioactive implant for repair and potential healing of cranial defects, J Neurosurg, vol. 120, pp. 273-277 (2014).

Heinemann, S. et al., Properties of injectable ready-to-use calcium phosphate cement based on water-immiscible liquid, Acta Biomaterialia, vol. 9, pp. 6199-6207 (2013).

European Search Report dated Oct. 23, 2019 from corresponding European Application No. 19175759.0.

\* cited by examiner

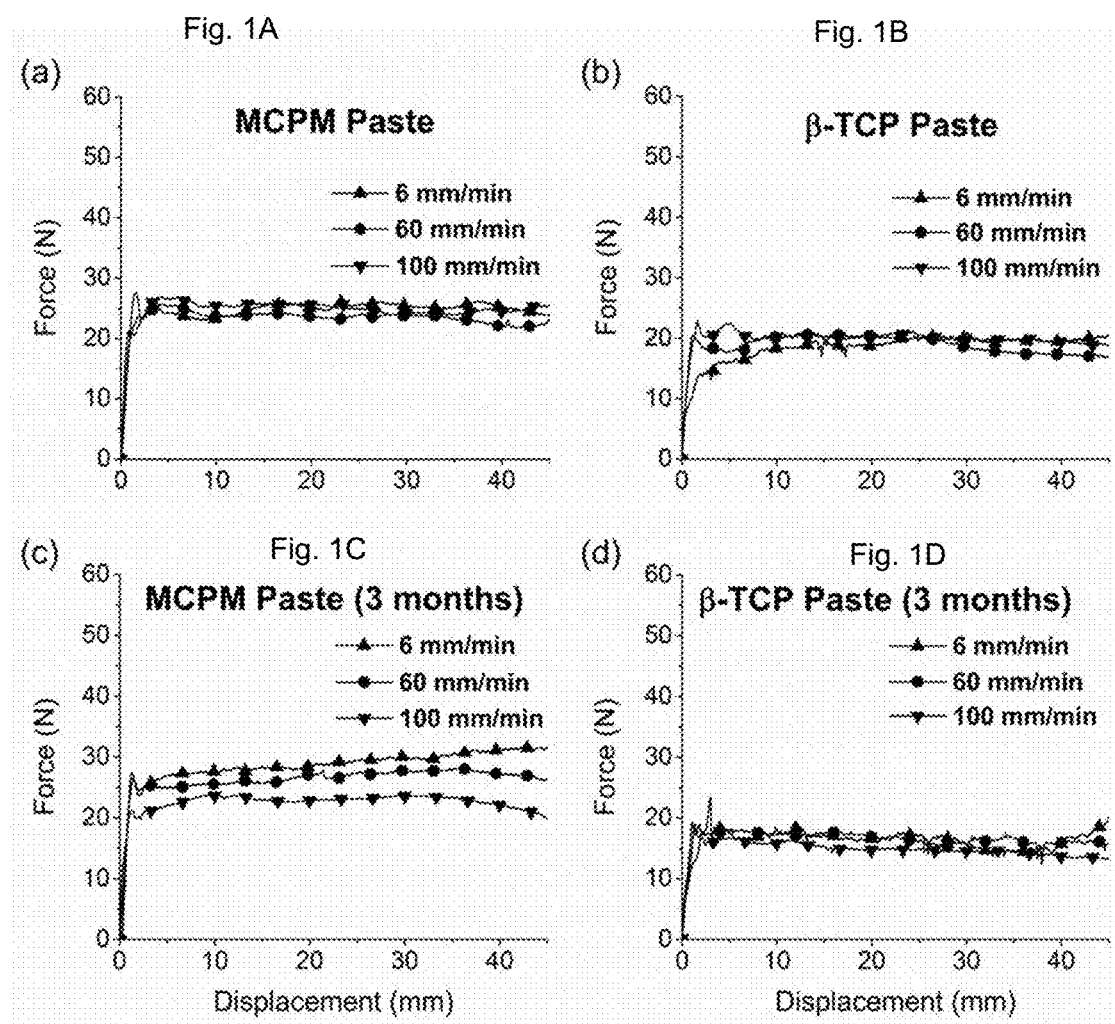

TWO-PASTE CEMENT-FORMING COMPOSITIONS

RELATED APPLICATION

The present application claims priority under 35 U.S.C. 119 of U.S. Application No. 62/674,195 filed May 21, 2018.

FIELD OF THE INVENTION

The present invention relates to two-paste cement-forming compositions, to articles of manufacture which contain such compositions, and to hardened cements formed from such compositions. The compositions are useful for bone repair or replacement.

BACKGROUND OF THE INVENTION

Calcium phosphate cements (CPCs) are commonly used as bone substitute materials due to their satisfactory biological performance in clinical applications. They have a chemical composition similar to the mineral phase of bone and exhibit osteoconductivity. Conventionally, there are two main CPCs: basic CPCs (i.e., apatite) and acidic CPCs (i.e., brushite/monetite). Brushite and monetite cements are formed by an acid-base reaction. They are most commonly produced by mixing a powder containing a slightly basic calcium phosphate such as β-tricalcium phosphate (β-TCP, β-$Ca_3(PO_4)_2$) and an acidic phosphate such as monocalcium phosphate monohydrate (MCPM, $Ca(H_2PO_4)_2.H_2O$) with water or an aqueous solution to form a paste, which can then be delivered into bone defects by injection. The paste then gradually sets into a hard solid in situ, for example, through entanglement of brushite crystals. Good injectability of such cements means that invasive surgical procedures can be avoided.

Acidic CPCs have attracted attention due to their ability to resorb faster than basic CPCs in vivo. Basic apatite cement is relatively chemically stable under physiological conditions and may still be present even after years in vivo. In contrast, acidic brushite and monetite can be resorbed within a few months, potentially permitting fast replacement of the material with the body's own bone, as has recently been observed in the skull (Engstrand et al., Development of a bioactive implant for repair and potential healing of cranial defects, *Journal of Neurosurgery*, 120(1):273-277 (2014)).

However, short working times and low mechanical strength has limited the clinical application of traditional acidic CPCs. In previous studies, the setting reaction was slowed down and the mechanical properties improved either by the addition of retardants (e.g., soluble pyrophosphates and/or citrates), by changing the reactant ratio, or by adjusting the particle size distribution of the starting powder. Nevertheless, the complex handling process may cause some important problems, such as the increased risk of contamination during preparation and difficulties in forming a homogenous and reproducible paste within a limited working time.

To address these problems, non-aqueous solvents were introduced to the starting powders of acidic CPCs to form premixed, i.e., ready-to-use, pastes which remain stable during storage and harden only after being in contact with water, for example when injected into bone defects. These premixed pastes are used in one- or two-phase systems to form acidic CPCs, for example, as described by Åberg et al., Premixed acidic calcium phosphate cement: characterization of strength and microstructure, *J Biomed Mater Res B Appl Biomater*, 93(2):436-41 (2010), and Chow et al., U.S. Pat. No. 9,259,439. In the one-phase system, the premixed pastes are prepared by stabilizing calcium phosphate-based reactants in a non-aqueous but water-miscible liquid such as glycerol or polyethylene glycol. One successful premixed acidic CPC was formulated by combining glycerol with a MCPM and β-TCP powder, a surfactant (polysorbate 20) and a gelling agent (hydroxypropyl methylcellulose). The paste can be injected directly into the bone defect and in contact with the body fluid. In vivo, the non-aqueous liquid is replaced by water through diffusion, and the paste sets into a hard mass over time. However, due to the inherent difficulties in eliminating moisture during manufacturing and storage, which causes the formation of monetite, the pastes typically have short shelf-life. Further, the slow penetration of body fluid into the cement often causes the interior of the cement paste to harden at a slower rate than the exterior, which weakens the mechanical properties of the set cements.

In the two-phase system, basic and acidic calcium phosphate-based reactants are mixed separately with a liquid phase (aqueous solution or water-miscible solvent) to form two different premixed pastes which can be mixed during injection through a mixing device. Interactive reactants are separated into different pastes, prolonging the shelf-life. At least one of the two pastes should be aqueous in order to trigger the setting reaction once all the components come into contact, without the need to take up water from the surrounding environment. Dual chamber syringes attached to a static mixer can be used in this system to ensure a swift and reproducible mixing process (i.e., seconds or tens of seconds), and decrease the risk of contamination since the mixture of the two pastes can be directly injected into bone defects after mixing.

Even though these CPCs are very attractive, some important disadvantages impede their optimal use in certain situations. When premixed pastes come in to contact with an aqueous environment, the weak cohesion of the pastes, commonly caused by the hydrophilicity of the pastes, high liquid to powder ratio, and/or high solubility of the reactants such as MCPM, increases the handling difficulty. The disintegration of CPCs in vivo leads to weak mechanical behavior of the final products and may also have negative biological effects, such as severe inflammatory responses, blood clotting, and cardiovascular complications.

Adequate shelf life, good water-resistance and mechanical strength of premixed acidic pastes are crucial in clinical applications. Heinemann et al., Properties of injectable ready-to-use calcium phosphate cement based on water-immiscible liquid, *Acta Biomater*, 9(4):6199-207 (2013), presented a one phase-system based on apatite cement with a better cohesion without sacrificing mechanical properties by combining calcium phosphate powders and a water-immiscible carrier liquid with suitable surfactants. During setting, a discontinuous liquid exchange was obtained in pastes to maintain the bulk properties of the cement. The obtained apatite cement retained the desirable mechanical strength of conventional CPC counterparts and showed improved cohesion and mechanical properties. However, the high reactivity between MCPM and β-TCP, and higher solubility of MCPM means that using a water-immiscible carrier liquid in the one phase-system based on acidic cements results in poor shelf life, water-resistance and mechanical strength.

Thus, a need exists for an injectable ready-to-use CPC composition that exhibits good cohesion, adequate shelf life, and sufficient mechanical properties to allow reliable delivery in vivo for optimal bone repair and replacement.

SUMMARY OF THE INVENTION

Accordingly, it is an object of the present invention to provide an injectable ready-to-use CPC composition that exhibits good cohesion, adequate shelf life, and sufficient mechanical properties to allow reliable delivery in vivo for use in bone repair and replacement.

In one embodiment, the invention is directed to an injectable, ready-to-use two paste cement-forming composition, comprising (a) a first paste comprising a non-aqueous oil-based suspension of monocalcium phosphate monohydrate (MCPM) powder, at least one surfactant effective to improve compatibility of the oil and the MCPM, and an organic acid, the first paste having an oil to MCPM powder weight ratio of about 0.2 to about 0.5, and (b) a second paste comprising an aqueous suspension of β-tricalcium phosphate (β-TCP) powder and a gel-forming polymer, the second paste having a water to β-TCP powder weight ratio of about 0.3 to about 0.5, wherein the molar ratio of β-TCP powder to MCPM powder is greater than 1.

In another embodiment, the invention is directed to a hardened cement formed by mixing the first paste and the second paste, and allowing the mixture to set.

In another embodiment, the invention is directed to an article of manufacture comprising the two-paste composition, wherein the article of manufacture comprises a first compartment in which the first paste is contained, and a second compartment in which the second paste is contained.

In another embodiment, the invention is directed to the two-paste composition for use as a bone repair or bone replacement material.

The two-paste compositions according to the invention exhibit a good combination of cohesion, shelf life, and mechanical properties that allow reliable delivery in vivo for use in bone repair and replacement. These and additional embodiments and advantages will be more fully understood in view of the following detailed description.

BRIEF DESCRIPTION OF THE DRAWINGS

The following detailed description and Examples will be more fully understood in view of the drawings, in which:

FIGS. 1A-1D show force vs. displacement curves obtained from (A) fresh MCPM paste in group M/0C, (B) fresh β-TCP paste, (C) MCPM paste in group M/80C, and (D) β-TCP paste stored for 3 months at 4° C., as described in the Examples.

DETAILED DESCRIPTION

Figures 2A, 2B, 2C:
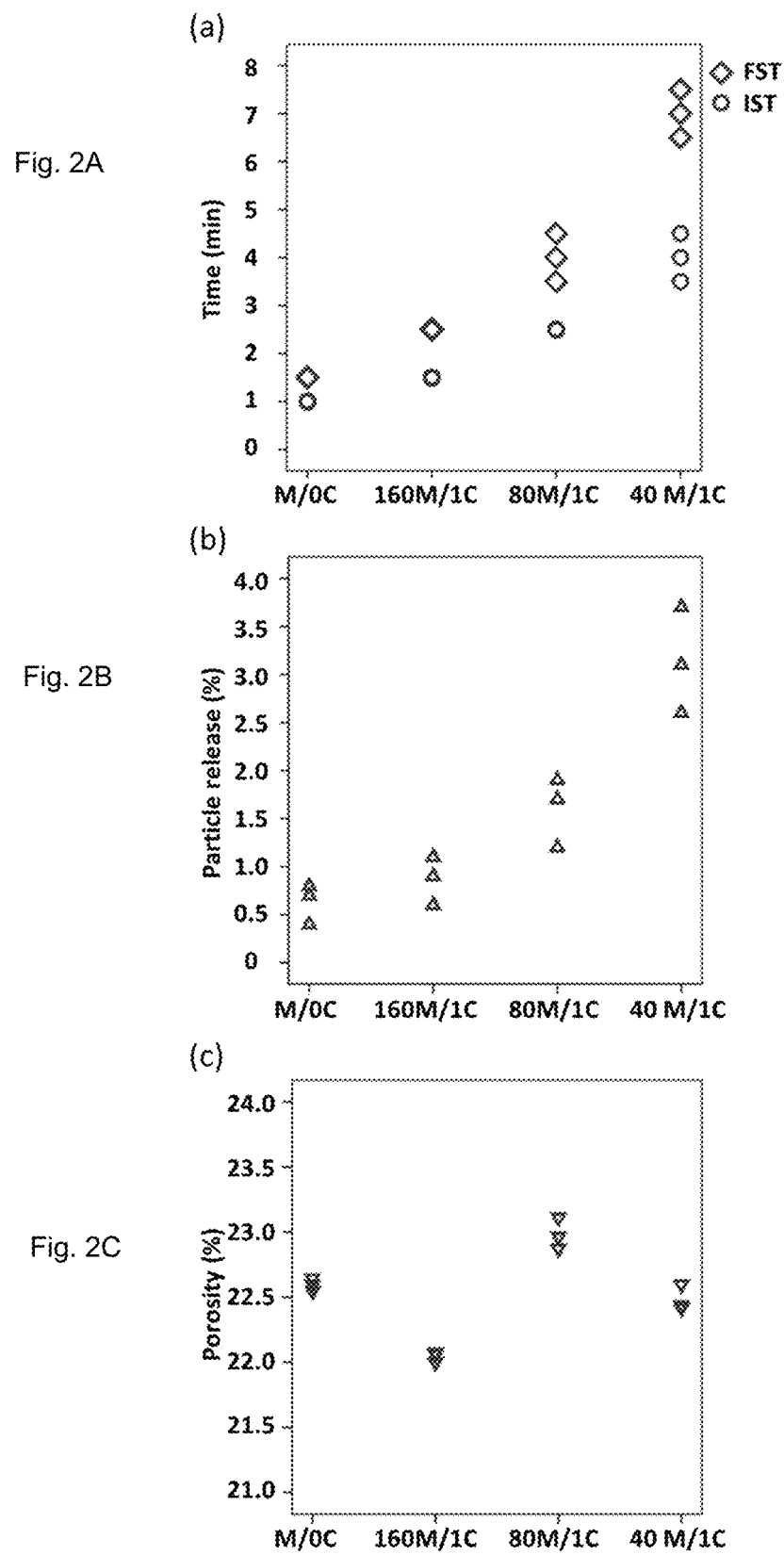
FIGS. 2A-2C show initial setting time (IST) and final setting time (FST), particle release, and porosity, respectively, of specimens as described in the Examples, with three measurements per group.

The two-paste compositions according to the invention exhibit a good combination of properties that allow reliable delivery in vivo for use in bone repair and replacement.

Importantly, the compositions according to the invention are injectable and ready-to-use, i.e., they can be easily mixed and injected without measuring or handling any individual components. Advantageously, manual transfer of components or mixture to a separate injection device can be avoided with the inventive compositions. The compositions therefore accommodate the surgical setting where a physician can access the compositions in the ready-to-use form, without additional handling or contamination of individual components, and deliver a composition to the site needing repair without delay. Additionally, since the compositions are readily deliverable, the compositions can be designed to set in a short period of time, avoiding undesirable delays in a surgery procedure.

The first paste included in the two paste cement-forming composition comprises a non-aqueous oil-based suspension of MCPM powder, at least one surfactant effective to improve compatibility of the oil and the MCPM, and an organic acid. The oil provides a vehicle to facilitate injectability of the MCPM paste and mixing of the MCPM powder with the β-TCP powder when the pastes are mixed and the composition is delivered to the bone repair or replacement site. Because the oil suspension is non-aqueous, thereby preventing the MCPM powder from premature reaction, the shelf-life of the cement-forming composition is increased, yet the composition is in a ready-to-use form. In certain embodiments, shelf life is greater than 3 months. Suitable oils include vegetable oils, such as monoglycerides, diglycerides and triglycerides. In a specific embodiment, the oil comprises a triglyceride, and, more specifically, a medium chain triglyceride having 6 to 12 (C6-C12) carbon atoms in the fatty acid moieties. In a more specific embodiment, the oil comprises a C8-C12 triglyceride.

The surfactant is effective to improve compatibility of the oil and the MCPM powder in the suspension, which further facilitates mixing of the MCPM powder and β-TCP powder when the pastes are mixed and the composition is delivered to the bone repair or replacement site. Nonionic, anionic and/or cationic surfactants may be employed. In a specific embodiment, nonionic and/or anionic surfactant is included in the first paste. In a further embodiment, both nonionic surfactant and anionic surfactant are included. Suitable nonionic surfactants include, but are not limited to, ethoxylated surfactants such as fatty alcohol ethoxylates, fatty acid ethoxylates, alkylphenol ethoxylates, ethoxylated amines, ethoxylated fatty acid amides, and terminally blocked ethoxylates (poloxamers), fatty acid esters of polyhydroxy compounds, sorbitol or glycerol, and amine oxides. In specific embodiments, the nonionic surfactant is a fatty acid ethoxylate, or, more specifically, castor oil ethoxylate. Suitable anionic surfactants contain a head anionic functional group, such as a sulfate, sulfonate, phosphate, or carboxylate. Examples include, but are not limited to, ammonium lauryl sulfate, sodium lauryl sulfate (sodium dodecyl sulfate, SLS, or SDS), and the related alkyl-ether sulfates such as sodium laureth sulfate (sodium lauryl ether sulfate or SLES), and sodium myreth sulfate, docusate (dioctyl sodium sulfosuccinate), alkyl-aryl phosphate, and alkyl phosphates. In specific embodiments, the anionic surfactant is an alkyl phosphate, or, more specifically, hexadecyl dihydrogen phosphate.

The organic acid is included in order to control the setting time. While acidic pastes are typically modified with organic acids to extend their short working times, undesirably long setting times can result. Surprisingly, in the two-paste compositions of the invention, the organic acid improves mechanical properties of hardened cement formed from the composition, without a significant delay in the setting time of the cement. Examples of suitable organic acids include, but are not limited to, lactic acid, citric acid, gluconic acid, itaconic acid, formic acid, acetic acid and malic acid. In a specific embodiment, the organic acid comprises citric acid.

In additional specific embodiments, the first paste comprises a glyceride oil, more specifically a triglyceride oil, more specifically, a medium chain triglyceride oil, or even more specifically, a C8-C12 triglyceride oil, a combination of nonionic and anionic surfactants, more specifically, a fatty acid ethoxylate and a alkyl phosphate, and citric acid. In more specific embodiments, the first paste comprises a C8-C12 triglyceride oil, a combination of castor oil ethoxylate and hexadecyl dihydrogen phosphate, and citric acid.

The weight ratio of oil to MCPM powder in the first paste is in a range of about 0.2 to about 0.5, or, more specifically, from about 0.3 to about 0.4, to provide good injectability/dispensing of the paste and to facilitate mixing of the MCPM powder with the β-TCP paste. The weight ratio of oil to surfactant may vary depending on the specific surfactant employed in order to obtain sufficient improvement in the compatibility of the oil and MCPM powder. In a specific embodiment, the weight ratio of oil to surfactant is about 10:1 to about 1:1 or, more specifically, about 5:1 to about 1:1. In a further specific embodiment, wherein a combination of nonionic and anionic surfactants are employed, the weight ratio of nonionic surfactant to anionic surfactant may be varied depending on the specific surfactant or surfactant combination employed in order to obtain sufficient improvement in the compatibility of the oil and MCPM powder. In a specific embodiment, the weight ratio of nonionic surfactant to anionic surfactant is about 3:1 to about 1:1. The weight ratio of MCPM powder to organic acid may be varied to optimize the setting time and mechanical strength for a particular use. In a specific embodiment, the weight ratio of MCPM powder to organic acid is about 160:1 to about 25:1, or about 100:1 to about 40:1.

The second paste comprises an aqueous suspension of β-TCP powder and a gel-forming polymer. The gel-forming polymer increases the viscosity and stability of the aqueous β-TCP paste, which improves the injectability of the paste and prevents filter pressing. Suitable gel-forming polymers include, but are not limited to, sodium hyaluronate, hydroxy propyl methylcellulose, cellulose acetate, poly(phenylene oxide), polyacrylonitrile, poly(methyl) methacrylate, poly (vinyl chloride) and poly(vinyl alcohol). In a specific embodiment, the gel-forming polymer comprises sodium hyaluronate. The second paste may optionally include oil or other nonaqueous liquid such as glycerol or polyethylene glycol, and/or surfactant as desired to further optimize the injectability of the second paste, and/or to facilitate mixing of the first and second pastes.

The second paste has a water to β-TCP powder weight ratio of about 0.3 to about 0.5, or, more specifically, from about 0.35 to about 0.45. The gel-forming polymer is included in an amount sufficient to increases the viscosity and stability of the aqueous β-TCP paste. In a specific embodiment, the second paste comprises about 0.01 to about 4 weight percent of the gel-forming polymer.

The molar ratio of β-TCP powder to MCPM powder is greater than 1 in order to provide sufficient mechanical strength to the hardened cement formed form the two-paste compositions of the invention. In a specific embodiment, molar ratio of β-TCP powder to MCPM powder is not greater than about 2.5 or, more specifically, not greater than about 2.0, or even more specifically, not greater than about 1.5, or, more specifically, is about 1.5.

The invention also encompasses a hardened cement formed from the compositions as described herein. The hardened cement is formed by mixing the first paste and the second paste and allowing the cement sufficient time to set. Initial setting may typically be achieved within 1 to 4 minutes, and final setting may typically be achieved within 1 to 10 minutes. Such short setting times are acceptable since the mixing of the pastes can be conducted adjacent to or at the site of injection and injection follows immediately after mixing, thereby avoiding delay in surgical procedures owing to long setting times.

Figure 8:
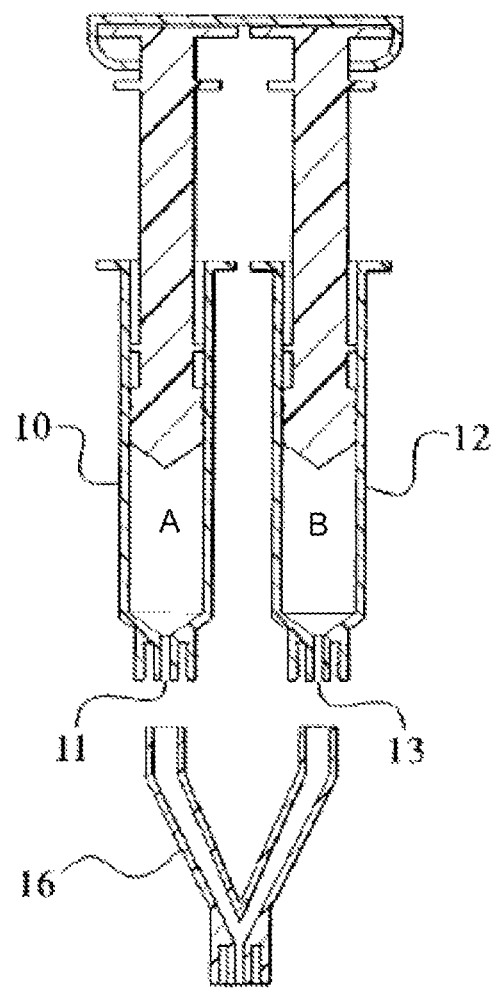
FIG. 8 shows one embodiment an article of manufacture according to the invention.

The invention is also directed to an article of manufacture comprising any of the compositions as described herein. The article of manufacture comprises a first compartment in which the first paste is contained, and a second compartment in which the second paste is contained. In a specific embodiment, as shown in FIG. 8, the first compartment 10 and the second compartment 12 are in the form of a two-compartment syringe, and the article of manufacture includes a first piston operable to dispense the first paste A from the first compartment at outlet 11 and a second piston operable to dispense the second paste B from the second compartment at outlet 13. The pistons can be actuated by respective actuators or a single actuator may be employed to operate both pistons. For example, the actuator can be operable to simultaneously actuate the first and second pistons to simultaneously dispense the first paste and the second paste from the first compartment and the second compartment. The article may further comprising a mixing chamber 16, for example including a mixing mechanism such as a static mixer, arranged to receive the first paste dispensed from the first compartment and the second paste dispensed from the second compartment. The mixture can then be dispensed from the mixing chamber to the surgical site.

The compositions are suitable for use in repairing or replacing bone. Thus, a further embodiment of the invention comprises a method for repairing or replacing bone. The method comprises delivering any of the compositions described herein to a site in need of bone repair or bone replacement. In a specific embodiment, the composition is delivered to the site by an article of manufacture as described above, for example, comprising a first compartment in which the first paste is contained, a second compartment in which the second paste is contained, and a mixing chamber arranged to receive the first paste dispensed from the first compartment and the second paste dispensed from the second compartment, wherein a mixture of the first paste and the second paste is delivered from the mixing chamber to the surgical site.

The following examples demonstrate embodiments of the invention.

EXAMPLES

These examples describe preparation of various compositions and aspects according to the invention. An exemplary system consisted of an MCPM paste and a β-TCP paste in a MCPM:β-TCP 45:55 molar ratio. The slight excess of β-TCP is known to give increased mechanical strength. A water immiscible liquid with two surfactants was employed as the liquid phase of the MCPM paste to improve the water balance in the paste and prolong the shelf life. Water was added to the β-TCP paste to initiate the setting reaction when mixed with the MCPM paste. Citric acid was used in this system as well.

Manual mixing of β-TCP (Sigma-Aldrich, USA) and 2 wt % sodium hyaluronate solution resulted in a β-TCP paste with a liquid to powder weight ratio of 0.4 g/g. The relatively high liquid to powder ratio ensured the availability of water for the setting reaction. The addition of the gel-forming polymer, sodium hyaluronate, which has good viscoelastic and hydrating properties in water, increases the viscosity and stability of the β-TCP paste, as well as prevents filter pressing and ensures a steady injectability.

Four types of MCPM pastes were produced, one consisting solely of MCPM (Scharlau, Spain) and a further three, containing varying amounts of citric acid (Sigma-Aldrich, USA) in the powder phase. These were placed in an oil-based suspension at an oil to powder ratio of 0.35 g/g. The MCPM:citric acid weight ratios of the powder phase in the three citric acid-containing samples were 160:1, 80:1 and 40:1. The groups were named after their weight ratios of MCPM and citric acid: M/0C, 160M/1C, 80M/1C and 40M/1C, respectively. The oil based suspension was composed of the synthetic short chain triglyceride Miglyol 812 with 8C-12C saturated fatty acids and two surface-active agents: castor oil ethoxylate 35 (Cremophor ELP, BASF, Germany) and hexadecyl dihydrogen phosphate (Cetyl-phosphate, Amphisol A, Brenntag AG, Germany), at an oil:castor oil ethoxylate:hexadecyl dihydrogen phosphate weight ratio of 15:3:2. The four MCPM pastes were prepared by mixing 40 g of the powder phase with 14 g of oil based suspension in a 125 mL zirconia beaker with 4 balls of 26 g each in a planetary ball mill (PM100, Retsch Corporation, Germany) for 6 h at 450 rpm. After ball milling, the particle size of MCPM was low enough to achieve homogeneous pastes. A lower liquid to powder ratio was used than for the β-TCP paste to avoid phase separation with time and provide good injectability. In the liquid phase, the water-immiscible carrier liquid provides a necessary unreactive lubricant and carrier liquid. Surfactants were used to promote compatibility of the polar mineral particles with the hydrophobic carrier liquid, as well as to promote stability of the MCPM paste.

Setting Time

The β-TCP and MCPM pastes were mixed together manually, at a 55:45 molar ratio of β-TCP:MCPM for 1 min before being molded in Teflon rings (12.5 mm in diameter and 5 mm in height). The specimens' surface was evaluated every 30 seconds using a 113 g Gillmore needle with a tip diameter of 2.12 mm to measure the initial setting time (IST) and a 453.5 g Gillmore needle with a tip diameter of 1.06 mm to measure the final setting time (FST), as indicated by the lack of visible marks on the specimen surface.

Injectability

The injectability of each paste was evaluated by monitoring simultaneously the extrusion force and plunger displacement of approximately 2.8 mL pastes extruded from a 3 mL syringe (BD Plastipak, Belgium) with an outlet diameter of 1.90 mm at different crosshead speeds in a universal testing machine (Shimadzu AGS-X, Japan).

Cohesion

A modified method to evaluate the cohesion properties of CPCs based on previous work was used. A commercially available brushite cement (chronOS™ Inject, Synthes GmbH, Switzerland) was also tested with the same method for comparison. ChronOS™ Inject is a biphasic cement with β-TCP granules embedded in a brushite cement matrix.

The β-TCP and MCPM pastes were manually mixed until homogeneity based on the 55:45 ratio for 30 s to form 1 g of paste mixture. 1 g paste of chronOS™ Inject cement was prepared by mixing the powder and liquid phases at a ratio of 0.315 mL/g for 30 s. The pastes were then injected through a syringe in 8 mL water 1 min from start of mixing. The specimens were photographed immediately after injection. After 24 h, the specimen status was recorded again. The chronOS™ Inject specimen had disintegrated after 24 h. The set specimens from the M/0C, 160M/1C, 80M/1C and 40M/1C groups were removed from the liquid, rinsed with 2 mL water and dried at 37° C. The entire liquid was centrifuged at 2500 g for 10 min. The separated precipitate was dried at 37° C. The mass of the set specimens and precipitates were weighed after drying.

Compressive Strength

The β-TCP and MCPM pastes were manually mixed at a 55:45 molar ratio of β-TCP:MCPM for 30 s to obtain a single, homogenous paste, after which the paste was placed into cylindrical moulds measuring 6 mm in diameter and 13 mm in height. Specimens were transferred into phosphate buffered saline solution (PBS, Sigma-Aldrich, St. Louis, Mo., USA, containing 0.01 M phosphate buffer, 0.0027 M potassium chloride and 0.137 M sodium chloride, pH 7.4) in sealed plastic containers at 37° C. for either 4 h or 24 h. The cement specimens were removed from the moulds and polished with 1200 grit SiC papers to achieve flat and parallel ends measuring 12 mm in height, according to the ASTM F451 standard for acrylic bone cements. Porosity was evaluated using six cement specimens from each group after setting for 24 h.

The compressive strength of cement specimens was measured using a universal testing machine (AGS-X, Shimadzu, Japan) at a cross-head speed of 1 mm/min until failure. To distribute the load evenly during the test, a thin plastic film was positioned between the specimen and the cross-head.

After the compressive strength test, the cement specimens were immediately immersed in liquid nitrogen to stop the setting reaction and remove the unreacted water.

Porosity

The porosity of cement specimens set for 24 h was calculated using their skeletal and apparent densities.

The apparent density of the cement specimens was obtained from Archimedes' principle. First, the apparent volume (Va) of the cement specimens was measured in double distilled water at room temperature using a balance (NewClassic MF ML 104, Mettler Toledo AB, 0.1 mg, Switzerland) equipped with a density kit (ML-DNY-43, Mettler-Toledo AB, Switzerland). Second, the cement specimens were dried in a vacuum chamber for 24 h. The mass of the dry specimens (Md) was measured, and the apparent density (Pa) was calculated according to $$\rho_a = \frac{m_d}{V_a} \quad (1)$$

The skeletal density (Ps) of the dry specimens was assessed three times by helium pycnometry (AccuPyc 1340, Micromeritics, USA, maximum pressure of 19.5 Psi, chamber size of 1 cm3) with 20 purges and 10 runs. Before the measurement, six dry cement specimens (6 mm in diameter, 12 mm in height) from each group were ground and homogenized.

The porosity (Ø) was calculated using the skeletal density and the apparent density (Pa) according to $$\emptyset(\%) = \left(1 - \frac{\rho_a}{\rho_s}\right) \times 100 \quad (2)$$

Microstructure

The microstructure of the dried and fractured cement surfaces was assessed by scanning electron microscopy (SEM, Merlin, Germany), with an accelerating voltage of 2.00 kV with an SE2 detector. Specimens were dried and sputtered with a thin Au/Pd coating for 30 s.

Phase Transformation

Dry cement specimens were ground into a fine powder and analyzed by X-ray diffraction using a Bruker D8 diffractometer (Cu-Kα irradiation) in a theta-theta setup with scanning diffraction angles (2θ) 5-60° in steps of 0.02° with 0.25 s per step and a rotation speed of 80 rpm. Quantitative evaluation of the phase composition was then analyzed by Rietveld refinement with BGMN software (www.bgmn.de) [31, 32] and a Profex (http://profex.doebelin.org) [33] user interface. The phases used in the refinement were MCPM from PDF #04-011-3010 [34], β-TCP from PDF #04-008-8714 [35], β-calcium pyrophosphate (β-CPP) from PDF #04-009-3876 [36], brushite from PDF #04-013-3344 [37], and monetite from PDF #04-009-3755 [38].

Shelf Life

The stability of 80M/1C MCPM pastes and β-TCP pastes were each assessed in a three-month shelf-life test at 4° C. After storage under parafilm seal for three months, the pastes were used for the injectability evaluation as described above. Chemical reactivity of the two pastes was also assessed by the setting time and the compressive strength of set cements prepared from these pastes (as methods described above).

Statistics

IBM® SPSS® Statistics v. 22 (IBM Corp., USA) was used to perform a one-way analysis of variance (ANOVA). Scheffe's post hoc test was used to identify significant differences ($p<0.05$) between groups. Welch's robust test of equality of means and Tamhane's post-hoc test were performed when homogeneity of variance could not be confirmed using Levene's test.

Results

Injectability

Both β-TCP and MCPM pastes could be fully injected from the syringe without filter pressing. Force vs. displacement curves (FIGS. 1A and 1B) demonstrate the injection process of these pastes. These show an initial rapid increase in the extrusion force, which gradually flattened to a plateau with some small fluctuations, indicating a stable injection process. The maximum force slightly increased with increasing plunger speed during the period of rapid force increase in the beginning of the injection process. However, after the curves transferred to the plateau region, the plunger speed showed little impact on the extrusion force. The extrusion force in the plateau region of β-TCP pastes and MCPM pastes was around 20 N and 30 N at all plunger rates, respectively. The MCPM pastes containing citric acid demonstrated similar injectability to the MCPM paste without citric acid and the extrusion force in the plateau region was also in the range of 20 to 30 N at all plunger rates.

Setting Time

The homogeneous β-TCP and MCPM pastes were moulded within a short time to ensure that the preparation process had only a minimal impact on the setting time test. As shown in FIG. 2A, without citric acid, specimens of group M/0C demonstrated the shortest initial (1 min) and final (1.5 min) setting times. The setting time increased with a corresponding increase in the amount of citric acid in the MCPM pastes. The specimens in group 40M/1C showed the longest initial (4 min) and final (7 min) setting times.

Cohesion

Figure 3:
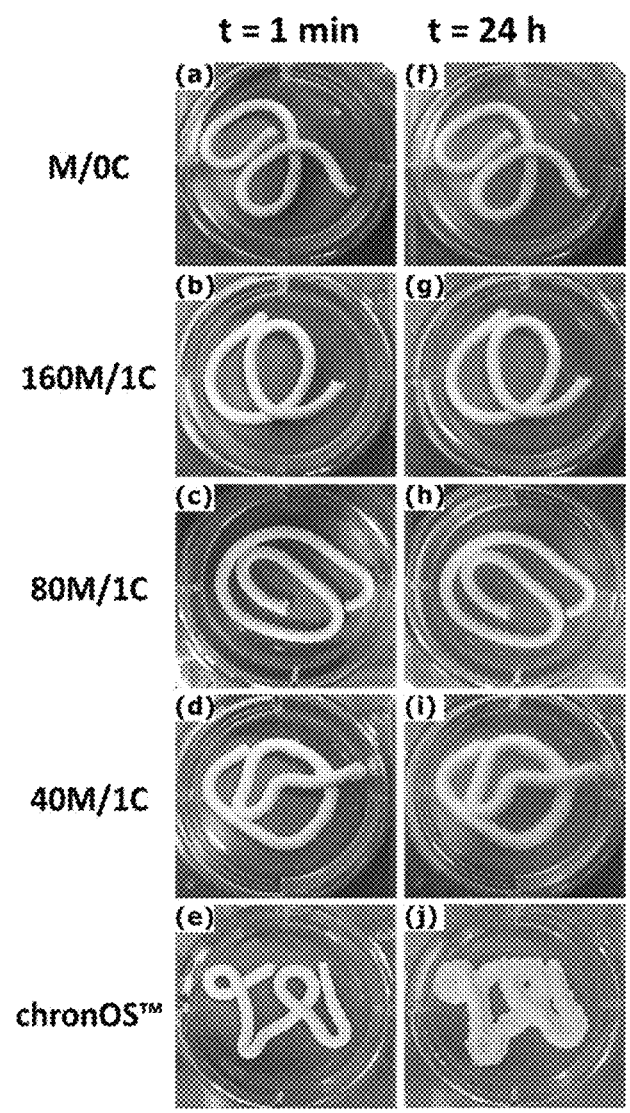
FIG. 3 shows images of specimens from compositions M/0C (a), 160M/1C (b), 80M/1C (c), 40M/1C (d) and chronOS™ Inject (e), all directly after injection, and from compositions M/0C (f), 160M/1C (g), 80M/1C (h), 40M/1C (i) and chronOS™ Inject (j), all after 24 h of incubation, as described in the Examples. The area of each well plate is 9.6 $cm^2$.

FIG. 3 shows all specimens directly after injection (a-e) and after 24 h of incubation (f-j). All specimens retained a tube-like shape after coming into contact with water for a short time (a-e). After 24 h of incubation, specimens from group M/0C, 160M/1C and 80M/1C retained their shape without signs of significant disintegration (f-h). However, some particles appeared to have been released from specimen group 40M/1C (i). ChronOS™ Inject paste lacked sufficient cohesion to set into a solid in water after 24 h, and showed the poorest cohesion (j). As shown in FIG. 2B, only 0.6±0.2 wt % of solids were released from the bulk specimen into the surrounding liquid in group M/0C. The released mass increased with a corresponding increase in citric acid, and 3.1±0.6 wt % was released from 40M/1C.

Compressive Strength

Figure 4:
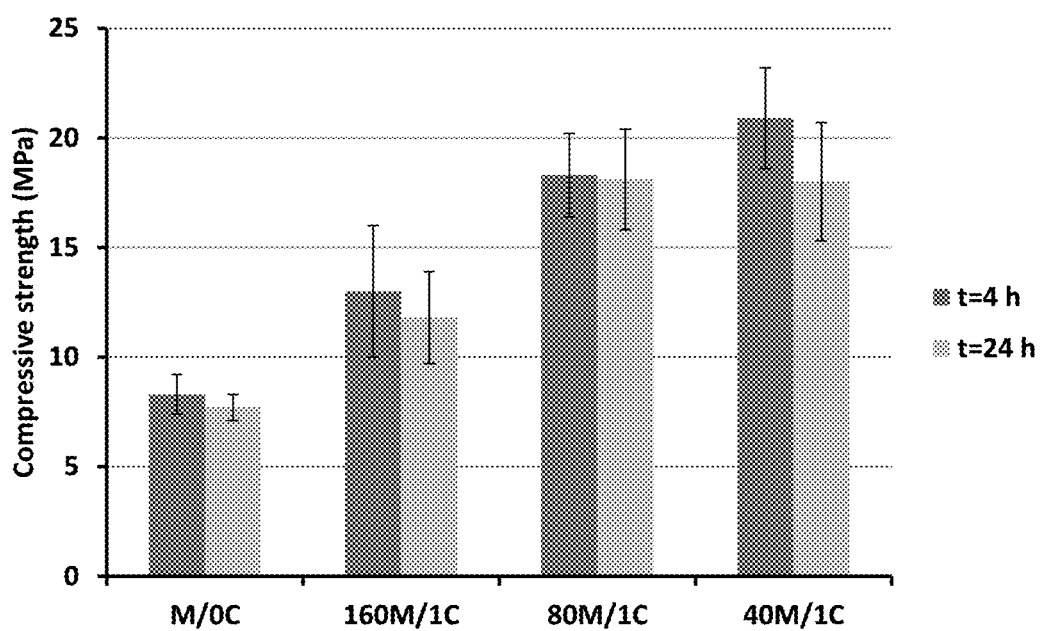
FIG. 4 shows compressive strength of specimens after 4 h and 24 h of incubation, as described in the Examples. Six measurements per group were obtained. The error bars represent standard deviations of the mean.

After 4 h of incubation in PBS solution, cement specimens in group M/0C showed the lowest compressive strength (FIG. 4, 8.3±0.9 MPa), whereas specimens in groups 80M/1C and 40M/1C showed the highest strength (FIG. 4, 18.3±1.9 and 20.9±2.3 MPa, respectively). While the compressive strength increased with an increasing amount of citric acid, it was not significant between cements 80M/1C and 40M/1C. There was no significant difference in compressive strength between the specimens set for 4 h and 24 h for any of the groups.

Porosity

As assessed by helium pycnometry, the porosity of the specimens was on average 22-23% for all groups (FIG. 2C).

Microstructure

Figure 5:
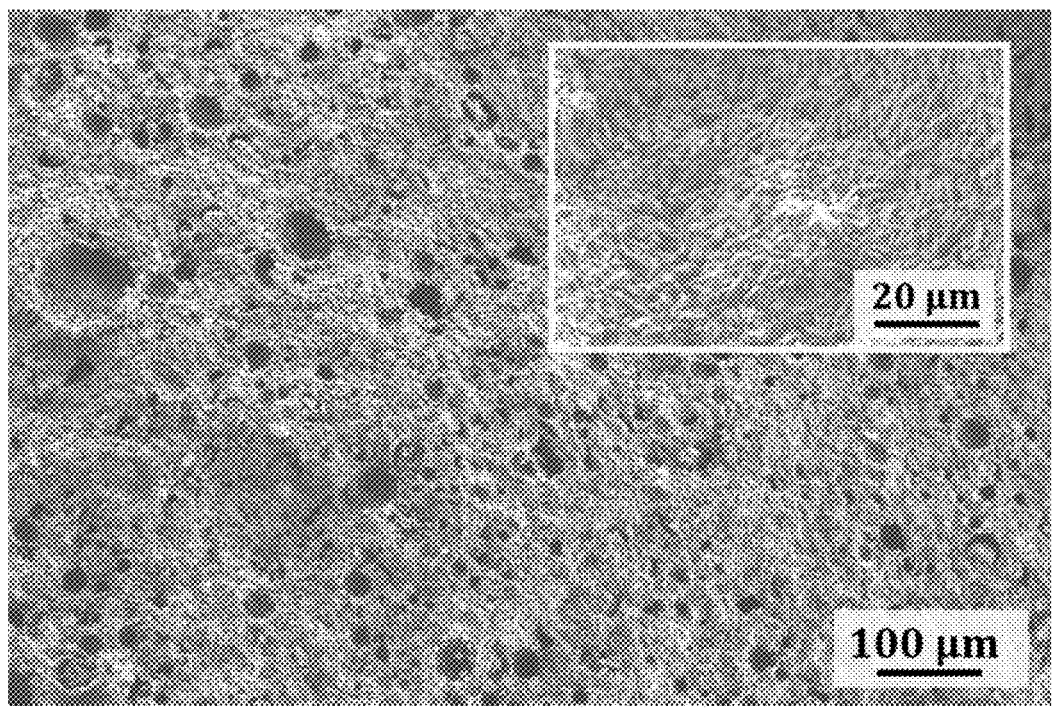
FIG. 5 shows SEM images of fractured surfaces of specimens from group 80M/1C after 4 h of incubation in PBS solution, as described in the Examples. The insert shows a higher magnification of the specimen.

The fractured surface microstructure of the cement specimen from group 80M/1C was evaluated by SEM (FIG. 5). Pores with diameters within the range of a few μm to 50 μm were evenly spread across the surface. Larger pores with a size of about 100 μm in diameter were also observed. The microstructure of fracture surfaces in the M/0C, 160M/1C and 40M/1C groups showed similar morphologies.

Phase Transformation

Figure 6:
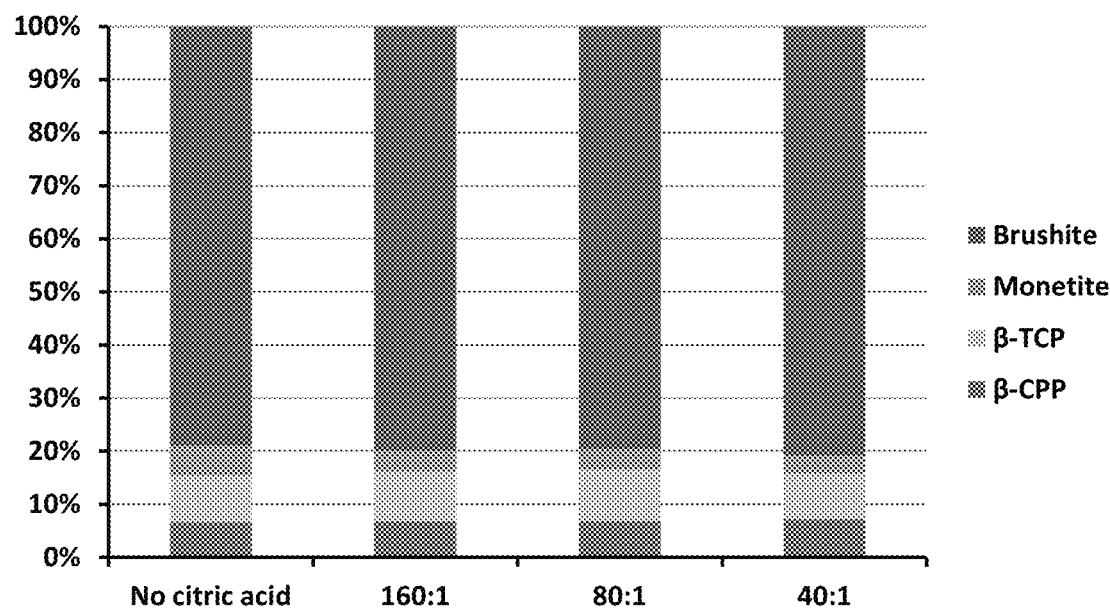
FIG. 6 shows phase composition of the set specimens after 4 hours from XRD and Rietveld refinement, as described in the Examples.

As shown in FIG. 6, after 4 h, all MCPM had reacted, and about 80 wt % of brushite had formed in all groups. After 24 h of incubation, the composition of the cement specimens had not changed (data not shown).

Shelf Life

Figure 7:
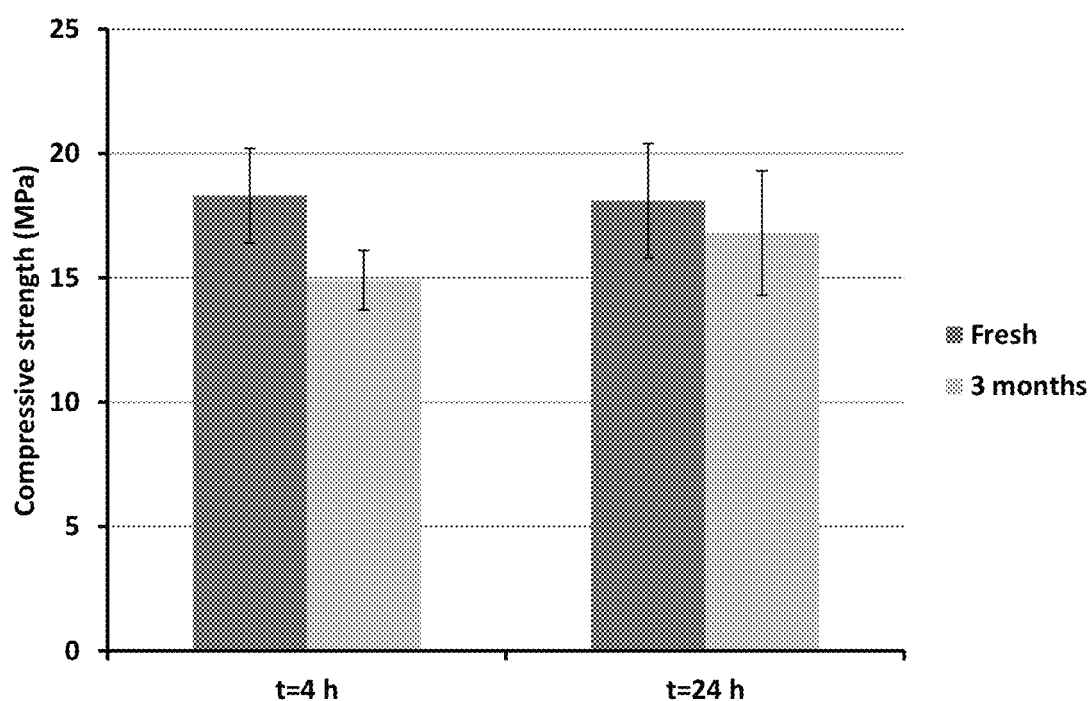
FIG. 7 shows compressive strength of specimens after 4 and 24 h of incubation made from the fresh pastes and pastes stored for 3 months from group 80M/1C, as described in the Examples. Six measurements per group were obtained. The error bars display standard deviations of the mean.

Both pastes were smooth and homogeneous, showing no oil separation after 3 months of storage. The extrusion force of the 80M/1C MCPM paste in the plateau region was around 20 N and 30 N at plunger speeds of 60 mm/min and 100 mm/min respectively (FIG. 1C). Compared with the fresh MCPM pastes (FIG. 1A), the extrusion force increased slightly after 3 months with a low plunger speed (6 mm/min). The injectability of the β-TCP pastes appeared virtually unchanged after 3 months (FIG. 1D) compared with the fresh β-TCP pastes (FIG. 1B). The setting time specimens demonstrated the same initial (2.5 min) and final (4±0.5 min) setting times compared with the specimens prepared by fresh pastes. As shown in FIG. 7, the cements made by the pastes stored for 3 months had a similar mechanical strength compared to the fresh ones.

Discussion

In the Examples, an injectable, ready-to-use two-phase system giving an acidic CPC cement is demonstrated. In the clinical application, the paste mixture would be obtained by mixing the two pastes through the dual chamber system, before coming into contact with body fluid by injection from a syringe. This requires that the two pastes have good cohesion as well as good and similar injectabilities. In addition, in a specific embodiment, the target setting time is preferably below 5 min as ready-to-use CPCs in the dual chamber system require shorter mixing times than conventional CPCs.

The injectability test demonstrated that increasing the extrusion speed had no significant impact on the injectability (FIGS. 1A and 1B) because of the shear thinning behavior of calcium phosphate pastes. Even at high plunger speeds (100 mm/min), the pastes showed no filter-pressing phenomenon. This enables a surgeon to mix in a precise and repeatable manner through the dual chamber system and deliver a cement forming composition in a minimally invasive manner.

The setting time directly affects the clinical procedure. Slow setting CPCs prolong the surgical process. For conventional CPCs, which are formed by mixing a powder with a liquid, a short setting time is linked to a short working time, i.e., it limits the period that surgeons can apply the cement during surgery, and can cause the cement to be unworkable before implantation if not performed successfully. Typically, 10-20 min may be a clinically acceptable setting time for conventional CPCs. However, the system consisting of two injectable pastes allows the dual chamber to be used, in which case the cement is mixed during injection. This allows the handling time and risk of contamination to be significantly reduced. It is therefore desirable for the ready-to-use CPCs to have faster setting times than conventional CPCs. The short handling time in combination with the virtually unlimited working time (unless the system is kept open) makes the short setting time (i.e., below 5 min) in this system feasible and an advantage for clinical use (FIG. 2A).

Citric acid is widely used as a setting retardant in brushite cement. It prolongs the setting time by chelating calcium ions. Hence, the cement devoid of citric acid showed the shortest setting time and those cements with increasing amounts of citric acid exhibited correspondingly longer setting times (FIG. 2A).

The paste mixture should have sufficient cohesion to avoid disintegration after coming into contact with aqueous environment in order to minimize the risk for complications and maximize its mechanical properties. In the β-TCP paste, the addition of sodium hyaluronate enhanced not only the viscosity, but also the anti-washout ability of the calcium phosphate pastes. In the MCPM paste, the hydrophobic oil carrier liquid with two surfactants was used. The oil phase, including a hydrophilic and a hydrophobic surfactant, significantly improve the cohesion properties of the paste.

After the MCPM and β-TCP pastes were mixed and immersed in water, the liquid phase of each paste improved the cohesion of the mixture in a short time. The hydrophilic surfactant accelerated the water-oil exchange in the MCPM paste to dissolve the MCPM. The dissolved MCPM effectively reacted with β-TCP in the surrounding area to form brushite crystals. Entanglement of the brushite crystals reinforced the cohesion property of the specimens during setting. The cements with shorter setting times generally have better cohesion since the cohesion of CPCs is a transient property. Therefore, a decrease in the final setting time due to a decreased amount of citric acid also showed an enhanced cohesion of the cements (FIGS. 2 and 3).

Brushite cement is usually considered to have low mechanical properties and high reactivity. However, the setting reaction typically takes one day until full completion, which is likely due to the pH of the paste increasing in the end of the setting reaction, which in turn decreases the reagents' solubility. During the setting reaction, brittle and plate-like brushite crystals grow rapidly to form an entanglement of crystals, which is responsible for the mechanical properties of set cement. While brushite cements generally fall in the range of trabecular bone compressive mechanical properties, it does not commonly meet trabecular bone properties under other loading scenarios, except for some experimental formulations. Brushite cements, similarly to other CPCs, are therefore generally indicated as non-load-bearing bone void filling materials.

The compressive strength and porosity of the cements have a strong negative correlation. In this study, cement specimens in all four groups had a similar porosity (FIG. 2C) and microstructure (FIG. 5). Despite this, there were some significant differences in the compressive strength between some of the groups. The mixing method and setting time affects the compressive strength of brushite cement, especially formulations with a short setting time. Manual mixing was applied in the present examples. However, a longer time is expected to be required for manual mixing to achieve a homogenous paste mixture than mixing through the dual chamber system. Even though the mixing and moulding process took less than 1 min, this delay may interrupt the entanglement of brushite crystals and lead to more defects during setting since the setting reaction starts immediately after mixing of the two pastes. The effect may be more severe in brushite cements with shorter setting times. Therefore, the increase in compressive strength was significant between the M/0C, 160M/1C and 80M/1C groups, which also had increasing setting times. There was no significant difference in strength between group 80M/1C and 40M/1C which was most likely due to the setting times of these two groups being long enough to satisfy the mixing process, in which the difference in amount of citric acid had no obvious effect.

No significant difference was found in the compressive strength of cement specimens set for 4 h and 24 h (FIG. 4). This is due to optimization of the composition based on preliminary studies. The MCPM dissolves fast due to the small particle size of the MCPM particles, and the hydrophilic surfactant in the MCPM paste accelerates the water-oil exchange after mixing the two pastes. This, in combination with the adequate water content in the β-TCP paste, was enough to guarantee a high degree of conversion, achieved even without water penetrating from the surrounding aqueous environment. Therefore, all the cement specimens reached their maximum strength in 4 h even with citric acid acting as a retardant in some groups (FIG. 4).

The compressive strength of human trabecular bone has been reported to lie between 0.1-14 MPa. This suggests that the 80M/1C and 40M/1C groups present higher values than human trabecular bone. However, group M/0C and 160M/

1C, with better cohesion properties, also show the potential for clinical applications, as their compressive strengths lie in the middle to upper range of human trabecular bone, sufficient for non-load-bearing applications, such as bone void fillers.

The 80M/1C group was used in the shelf life test since it showed both good compressive strength and cohesion properties. The MCPM paste and β-TCP paste showed stable chemical reactivity, with no significant changes in the setting time and compressive strength after 3 months. The β-TCP paste also demonstrated stability in the injectability test after 3 months of storage. The injection force of the MCPM paste was slightly increased after 3 months with low plunger speed (6 mm/min), but the increase was not obvious with higher plunger speeds (60 mm/min and 100 mm/min) because the viscosity of calcium phosphate pastes decreases with increased plunger speeds. It revealed that both pastes could potentially be used in the dual chamber system after 3 months.

CONCLUSION

Thus, a ready-to-use two-phase system based on brushite cement is provided. The two-phase system is injectable and can be used in a dual chamber system for simplified and fast filling of bone defects in a minimally invasive manner. By adding a suitable amount of retardants, a good cohesion, compressive strength and adequate shelf life were achieved, especially in the 80M/1C group. With the help of the dual chamber system, this formulation can greatly facilitate clinical applications by reducing surgery time, decreasing the risk of contamination, and ensuring repeatable results.

The various examples and embodiments described herein are exemplary only and are not to be construed as limiting the scope of the invention defined by the following claims. Throughout this specification, when a range of conditions or a group of substances is defined with respect to a particular characteristic (e.g., temperature, pressure, amounts, and the like) of the present invention, the present invention relates to and explicitly incorporates every specific member and combination of subranges or subgroups therein. Any specified range or group is to be understood as a shorthand way of referring to every member of a range or group individually as well as every possible subrange and subgroup encompassed therein; and similarly with respect to any subranges or subgroups therein.

What is claimed is:

1. An injectable, ready-to-use two paste cement-forming composition, comprising
   (a) a first paste comprising a non-aqueous oil-based suspension of monocalcium phosphate monohydrate (MCPM) powder, at least one surfactant effective to improve compatibility of the oil and the MCPM, and an organic acid, the first paste having an oil to MCMP powder weight ratio of about 0.2 to about 0.5, and
   (b) a second paste comprising an aqueous suspension of β-tricalcium phosphate (β-TCP) powder and a gel-forming polymer, the second paste having a water to β-TCP powder weight ratio of about 0.3 to about 0.5, wherein the molar ratio of β-TCP powder to MCPM powder is greater than 1.

2. The composition of claim 1, wherein the oil comprises C8-C12 triglyceride, and the at least one surfactant comprises at least one nonionic surfactant and at least one anionic surfactant.

3. The composition of claim 2, wherein the weight ratio of oil to surfactant is about 10:1 to about 1:1.

4. The composition of claim 2, wherein the weight ratio of nonionic surfactant to anionic surfactant is about 3:1 to about 1:1.

5. The composition of claim 2, wherein the at least one surfactant comprises castor oil ethoxylate and the at least one anionic surfactant comprises hexadecyl dihydrogen phosphate.

6. The composition of claim 1, wherein the organic acid comprises citric acid.

7. The composition of claim 1, wherein the weight ratio of MCMP powder to organic acid is about 160:1 to about 25:1, or about 100:1 to about 40:1.

8. The composition of claim 1, wherein the first paste has an oil to MCMP powder weight ratio of about 0.3 to about 0.4.

9. The composition of claim 1, wherein the gel-forming polymer comprises sodium hyaluronate.

10. The composition of claim 1, wherein the second paste comprises about 0.01 to about 4 weight percent of the gel-forming polymer.

11. The composition of claim 1, wherein the second paste has a water to β-TCP powder weight ratio of about 0.35 to about 0.45.

12. The composition of claim 1, wherein the molar ratio of β-TCP powder to MCPM powder is not greater than about 2.5, not greater than about 2.0, or not greater than about 1.5.

13. A hardened cement formed from the composition of claim 1, by mixing the first paste and the second paste, and allowing the mixture to set.

14. An article of manufacture comprising the composition of claim 1, wherein the article of manufacture comprises a first compartment in which the first paste is contained, and a second compartment in which the second paste is contained.

15. The article of manufacture of claim 14, wherein the first compartment and the second compartment are in the form of a two-compartment syringe, and the article of manufacture includes a first piston operable to dispense the first paste from the first compartment and a second piston operable to dispense the second paste from the second compartment.

16. The article of manufacture of claim 15, further comprising a mixing chamber arranged to receive the first paste dispensed from the first compartment and the second paste dispensed from the second compartment.

17. The article of manufacture of claim 15, further including an actuator operable to simultaneously actuate the first and second pistons to simultaneously dispense the first paste and the second paste from the first compartment and the second compartment.

18. A method for repairing or replacing bone, comprising delivering the composition of claim 1 to a site in need of bone repair or bone replacement.

19. The method of claim 18, wherein the composition is delivered to the site by an article of manufacture comprising a first compartment in which the first paste is contained, a second compartment in which the second paste is contained, and a mixing chamber arranged to receive the first paste dispensed from the first compartment and the second paste dispensed from the second compartment, wherein a mixture of the first paste and the second paste is delivered from the mixing chamber.

* * * * *